(12) United States Patent
Catalucci et al.

(10) Patent No.: US 12,357,572 B2
(45) Date of Patent: Jul. 15, 2025

(54) POWDER COMPOSITION BASED ON MICROPARTICLES EMBEDDING NANOPARTICLES FOR THE DELIVERY OF THERAPEUTIC/DIAGNOSTIC COMPOUNDS

(71) Applicants: CONSIGLIO NAZIONALE DELLE RICERCHE, Rome (IT); PLUMESTARS S.R.L., Parma (IT)

(72) Inventors: Daniele Catalucci, Segrate (IT); Michele Iafisco, Castel Maggiore (IT); Paolo Colombo, Parma (IT); Eride Quarta, Parma (IT)

(73) Assignees: Consiglio Nazionale Delle Ricerche, Rome (IT); Plumestars S.R.L., Parma (IT)

( * ) Notice: Subject to any disclaimer, the term of this patent is extended or adjusted under 35 U.S.C. 154(b) by 0 days.

(21) Appl. No.: 18/024,821

(22) PCT Filed: Sep. 9, 2021

(86) PCT No.: PCT/IB2021/058184
§ 371 (c)(1),
(2) Date: Mar. 6, 2023

(87) PCT Pub. No.: WO2022/053955
PCT Pub. Date: Mar. 17, 2022

(65) Prior Publication Data
US 2023/0390203 A1    Dec. 7, 2023

(30) Foreign Application Priority Data
Sep. 9, 2020    (IT) .................. 102020000021292

(51) Int. Cl.
| | | |
|---|---|---|
| *A61K 9/00* | (2006.01) | |
| *A61K 9/16* | (2006.01) | |
| *A61K 47/02* | (2006.01) | |
| *A61K 47/26* | (2006.01) | |
| *B82Y 5/00* | (2011.01) | |
| *B82Y 30/00* | (2011.01) | |
| *B82Y 40/00* | (2011.01) | |

(52) U.S. Cl.
CPC .......... *A61K 9/1611* (2013.01); *A61K 9/0075* (2013.01); *A61K 9/1623* (2013.01); *A61K 9/1682* (2013.01); *B82Y 5/00* (2013.01); *B82Y 30/00* (2013.01); *B82Y 40/00* (2013.01)

(58) Field of Classification Search
CPC .. A61K 9/0075; A61K 9/1611; A61K 9/1623; A61K 9/1694; A61K 47/26; B82Y 5/00; B82Y 30/00
See application file for complete search history.

(56) References Cited

U.S. PATENT DOCUMENTS

2016/0068554 A1    3/2016  Rusin et al.

FOREIGN PATENT DOCUMENTS

| EP | 2297172 | A2 | | 3/2011 |
|---|---|---|---|---|
| EP | 2898894 | A1 | | 7/2015 |
| EP | 2729180 | | * | 1/2019 |
| WO | 2009137595 | A2 | | 11/2009 |

OTHER PUBLICATIONS

Tsapis et al, Trojan particles, Large porous carriers of nanoparticles for drug delivery, PNAS, Sep. 2002, vol. 99, No. 19, pp. 12001-12005 (Year: 2002).*

Torge et al (The influence of mannitol on morphology and disintegration of spray-dried nano-embedded microparticles, European Journal of Pharmaceutical Science, 104 (2017), pp. 171-179. (Year: 2017).*

* cited by examiner

*Primary Examiner* — Mina Haghighatian
(74) *Attorney, Agent, or Firm* — Elmore Patent Law Group, P.C.; Joseph C. Zucchero; Carolyn S. Elmore (57) ABSTRACT

This invention relates to a powder composition for inhalation use comprising a plurality of microparticles comprising at least one water-soluble pharmaceutically acceptable carrier embedding at least one nanoparticle of calcium phosphate for the delivery of therapeutic/diagnostic compounds.

6 Claims, 6 Drawing Sheets

POWDER COMPOSITION BASED ON MICROPARTICLES EMBEDDING NANOPARTICLES FOR THE DELIVERY OF THERAPEUTIC/DIAGNOSTIC COMPOUNDS

The project that led to this application received funding from the European Union's Horizon 2020 CUPIDO research and innovation program under grant agreement n. 720834.

FIELD OF INVENTION

This invention relates to a powder composition for inhalation use comprising a population of microparticles comprising at least one water-soluble pharmaceutical carrier embedding at least one nanoparticle of calcium phosphate for the delivery of therapeutic/diagnostic compounds.

STATE OF THE ART

Medicinal products based on calcium phosphate nanoparticles for medical use capable of conveying therapeutic/diagnostic compounds to an organ are known and are being progressively developed, in order to therapeutically treat in a selective and effective way a determined pathological condition in a patient.

For example, WO 2016/102576 describes the preparation of a product comprising one or more negatively surface-charged calcium phosphate nanoparticles having a $\xi$-potential in the range of −41.0 mV to −27.0 mV comprising the steps of: a) maintaining a mixture having a pH between 7 and 10 and comprising an aqueous solution of calcium ions, an aqueous solution of phosphate ions and a solution of citrate ions at a temperature between 20° C. and 40° C. and for a time between 30 seconds and 10 minutes; b) removing the unreacted ions from the solution of phase a), thus obtaining a suspension of one or more calcium phosphate nanoparticles; c) recovering the product of one or more calcium phosphate nanoparticles from the suspension of phase b). The product of the invention can be used as a carrier for one or more diagnostic/therapeutic compounds for the treatment of pathologies such as cardiovascular diseases.

An aerosol is defined as a fine dispersion of particles (solid or liquid) in the air and in the field of pharmaceutical technologies aerosols by inhalation are promising means of administration under study also in regard to nanoparticle-based medicines, since they allow to exploit the lungs also as a site of absorption of drugs with systemic action, as well as for the local treatment of diseases such as asthma, chronic obstructive pulmonary disease, lung infections etc.

However, the Applicant noted that the use of inhalation aerosols for the administration of nanoparticle materials capable of conveying therapeutic/diagnostic compounds requires the use of suitable dispensing devices (inhalers) that impose constraints on their dosage and emission, as well as still having technical and functional limits of a dual nature, which still need to be addressed and mutually balanced.

From a first point of view, there is in fact the need to adequately control and optimize the phenomena of pulmonary deposition of the particles of the aerosol itself (a characteristic generally referred to as "respirability"), as particles of too small size after inhalation do not settle in the lung and are easily exhaled. The Applicant found that this phenomenon may lead to an ineffective administration of the drug and/or the need to resort to the emission and inhalation by the patient of greater quantities of aerosols, thereby negatively impacting on the costs and effectiveness of therapeutic treatment.

From another point of view, there are also other characteristics of nanoparticle materials that may preclude their effective administration by inhalation aerosol. Nanoparticles, in fact, can easily undergo aggregation phenomena and this makes it difficult either to dose or dispense, as it alters the aerodynamic properties of the aerosol in an uncontrollable way. In addition, aggregation phenomena in nanoparticle materials can have a negative impact on the effectiveness of their administration and, since they alter the dimensional and surface characteristics of the nanoparticles, compromise their correct pulmonary deposition and effective absorption by the patient's body and, consequently, also the conveyance of therapeutic/diagnostic compounds to the target site.

The Applicant has found that there are and are being tested technologies aimed at improving the respirability characteristics of nanoparticles that involve the incorporation into micrometric matrices (to obtain the so-called "nano embedding microparticles", NEM).

However, the Applicant found that the use of these technologies does not solve the issue but rather favor the aggregation of nanoparticles, therein compromising their dimensional and surface characteristics and therefore the correct pulmonary deposition and effective absorption by the patient's body and, consequently, the ability to convey therapeutic/diagnostic compounds to the target site.

The primary purpose of the present invention is therefore to identify a composition to effectively administer to a patient by inhalation nanoparticles for medical use able to convey therapeutic/diagnostic compounds to a target site, so as to overcome the technical and functional limits mentioned above.

SUMMARY OF THE INVENTION

In accordance with the present invention, the Applicant has surprisingly found that these desired characteristics can be achieved by identifying a specific type of matrix in which to incorporate calcium phosphate nanoparticles that already comprise one or more therapeutic/diagnostic compounds, thus obtaining a composition in the form of micronized powder particularly suitable to be used to effectively administer to a patient by inhalation nanoparticles for medical use able to convey therapeutic/diagnostic compounds to a target site.

Thus, in a first aspect thereof, the present invention refers to a powder composition comprising microparticles comprising a matrix of at least one pharmaceutically acceptable water-soluble carrier embedding at least one nanoparticle of calcium phosphate comprising one or more therapeutic/diagnostic compounds, for use as a medicament in which said powder is administered by inhalation.

Thanks to the incorporation of calcium phosphate nanoparticles that comprise one or more therapeutic/diagnostic compounds in a matrix of at least a pharmaceutically acceptable water-soluble carrier, the powder composition according to the present invention, in fact, allows to effectively administer by inhalation nanoparticles for medical use able to convey therapeutic/diagnostic compounds, guaranteeing an high yield of pulmonary deposition of them and preventing aggregation of the nanoparticles themselves, even at the site of deposition, ensuring thus an adequate absorption of therapeutic/diagnostic compounds and their effective delivery to the target site.

The inventors have in fact surprisingly discovered that using a pharmaceutically acceptable water-soluble carrier is possible to effectively incorporate calcium phosphate nanoparticles that already comprises one or more therapeutic/diagnostic compounds thus obtaining microparticles of suitable size for generate an aerosol by inhalation characterized by high respirability, thereby allowing an effective administration and deposition at the pulmonary level in the patient. Once microparticles are deposited, the matrix of pharmaceutically acceptable water-soluble carrier efficiently dissolves releasing nanoparticles, which are advantageously get back in dispersed form and with the desired surface and dimensional characteristics and can effectively convey the therapeutic/diagnostic compound to the site target.

The inventors have in fact surprisingly discovered that the specific interaction between the pharmaceutically acceptable water-soluble carrier and the nanoparticle of calcium phosphate in the presence of one or more therapeutic/diagnostic compounds allows on one hand to prevent aggregation phenomena during the preparation of the microparticle itself, thus contributing to obtain microparticles with characteristics suitable for their respirability, and on the other hand, prevents phenomena of aggregation of nanoparticles after the dissolution of the matrix at the site of pulmonary deposition.

In this way, the composition according to the present invention advantageously allows the administration by aerosol through inhalation of calcium phosphate nanoparticles comprising one or more therapeutic/diagnostic compounds and at the same time to make them readily available at the deposition site after dissolution of the matrix that incorporates them with the right dimensions and surface characteristics to be able to effectively convey therapeutic/diagnostic compounds to the target site.

Under a further and advantageous aspect, the present invention regards the composition in the form of powder according to the first aspect of the present invention, for use in the treatment of cardiovascular diseases, respiratory diseases, as well as for use as an immunostimulant substance.

The powder composition according to the present invention, when used as a medicament, for example, in the treatment of cardiovascular diseases, is administered by inhalation.

The properties of the composition in the form of powder according to the present invention make it particularly advantageous to be administered by inhalation as a dry powder.

The present invention, therefore, in a further aspect concerns an inhalation device comprising a container containing a powder composition according to the present invention.

Conveniently, the powder composition according to the present invention has the additional advantage of being obtainable by a simple and highly reproducible method. This contributes to making the production of the composition according to the present invention economically competitive.

In a further aspect, the present invention therefore concerns a method for the preparation of the powder composition according to the first aspect of the present invention, comprising the steps of:
providing a first aqueous dispersion of calcium phosphate nanoparticles comprising one or more therapeutic/diagnostic compounds;
dissolving in the dispersion of phase a) at least one pharmaceutically acceptable carrier soluble in water, in order to obtain a second aqueous dispersion,
spray-drying the aforementioned second aqueous dispersion.

BRIEF DESCRIPTION OF THE FIGURES

In the drawings:
FIG. 1 shows the microparticles of Example 1 analyzed by SEM (1a) and dissected by Focus Ion Beam (1b);
FIG. 2 shows the microparticles of Example 2 analyzed by SEM (2a) and dissected by Focus Ion Beam (2b);
FIG. 3 shows the microparticles of Example 3 analyzed by SEM (3a) and dissected by Focus Ion Beam (3b);
FIG. 4 shows the microparticles of example 4 analyzed by SEM (4a) and dissected by Focus Ion Beam (4b);
FIG. 5 shows the microparticles of example 5 analyzed by SEM (5a) and dissected by Focus Ion Beam (5b); and
FIG. 6 shows the microparticles of Example 6 analyzed by SEM (6a) and dissected by Focus Ion Beam (6b).

DETAILED DESCRIPTION OF THE INVENTION

In the context of the present invention, a new composition has been identified to effectively administer nanoparticles for medical use to a patient by inhalation capable of conveying therapeutic/diagnostic compounds, to overcome the technical and functional limits of the known art.

More specifically, the present invention, in a first aspect thereof, refers to a powder composition comprising microparticles comprising a matrix of at least one water-soluble pharmaceutically acceptable carrier embedding at least one nanoparticle of calcium phosphate comprising one or more therapeutic/diagnostic compounds, for use as a medicament in which said powder is administered by inhalation.

Within the scope of this description and in the subsequent claims, all numerical quantities indicating quantities, parameters, percentages, and so on are to be considered preceded in all circumstances by the term "approximately" unless otherwise indicated. In addition, all numerical quantity ranges include all possible combinations of maximum and minimum numerical values and all possible intermediate ranges, in addition to those specifically indicated below.

In the present invention when using the definition:
"microparticle" means a particle with a volume diameter of less than 10 µm;
"nanoparticle" means a particle with a volume diameter of less than 300 nm;
"pre-dosed dose" (hereinafter also referred to as "MD"), means the mass of powder composition loaded into a device for inhaling a powder composition by aerosol (inhaler). Usually this composition is loaded into a cartridge, or hard capsule;
"emitted dose" (hereinafter also referred to as "ED"), means the amount of pre-dosed dose emitted by the inhaler, following an inhalation act. The dose emitted is measurable according to the method of the European Pharmacopoeia 9.0 chapter 2.9.18, using the impactors Fast Screening Impactor and Next Generation Impactor.
"emitted fraction" (hereinafter also referred to as "EF"), means the ratio of the dose emitted and the dose pre-dosed, i.e. the ED/MD ratio;
"aerodynamic diameter" means the diameter of a sphere of unit density that has the same sedimentation rate as the actual particle under consideration. This value can be measured by applying the method described in the European Pharmacopoeia 9.0 chapter 2.9.18, using the impactors Fast Screening Impactor and Next Generation Impactor;

"median mass aerodynamic diameter" (hereinafter also referred to as "MMAD"), means the median of the distribution of the aerodynamic diameter of the particles of the powder composition;

"geometric standard deviation" (herein after also referred to as "GSD"), means the dispersion of the distribution data of the aerodynamic diameter of the particles of the composition in the form of powder around the median (MMAD);

"projection diameter" means the equivalent spherical diameter corresponding to the diameter of the circle owing the same projection area on a plane as the particle, determined by any suitable microscopic technique (e.g. with a Scanning Electron Microscope);

"fine particles" (hereinafter also referred to as "FP") means particles with an aerodynamic diameter of less than 5.0 µm;

"extra-fine particles" (hereinafter also referred to as "EFP") means particles with an aerodynamic diameter of less than 3.0 µm;

"fine particle dose" (hereinafter also referred to as "FPD"), means the quantity of fine particles of a powder composition;

"extra-fine particles dose" (hereinafter also referred to as "EFPD"), means the quantity of extra-fine particles of a powder composition;

"fine particle fraction" (hereinafter also referred to as "FPF"), means the ratio of the dose of fine particles to the dose emitted, i.e. the FPD/ED ratio;

"extra-fine particle fraction" (hereinafter also referred to as "EFPF"), means the ratio between the dose of extra-fine particles and the dose emitted, i.e. the EFPD/ED ratio;

"volume diameter" means the diameter of a perfect sphere having the same volume as the particle under analysis. The volume diameter is measurable by a laser light diffraction method.

"$Dv_{50}$" (hereinafter also referred to as "median volume diameter" or "VMD") means the median of the volume diameter distribution of a plurality of particles under analysis;

"$Dv_{10}$" means the 10th percentile of the distribution of volume diameters of a plurality of particles under analysis. It is the diameter below which is 10% of the particles of the sample taken into analysis;

"$Dv_{90}$" means the 90th percentile of the volume diameter distribution of a plurality of particles under analysis. It is the diameter below which 90% of the particles of the sample taken into analysis are located;

"high respirability" means a powder composition having FPF greater than 0.5;

Thanks to the incorporation of calcium phosphate nanoparticles comprising one or more therapeutic/diagnostic compounds in a matrix of at least one pharmaceutically acceptable water-soluble carrier, the composition in form of powder according to the present invention, in fact, allows to effectively administer by inhalation nanoparticles for medical use capable of conveying therapeutic/diagnostic compounds, ensuring a high yield of pulmonary deposition of the same and preventing aggregation phenomena of the nanoparticles themselves, even at the deposition site, thus ensuring adequate absorption of the therapeutic/diagnostic compounds and their effective delivery to the target site.

The inventors have in fact surprisingly discovered that using a pharmaceutically acceptable water-soluble carrier it is possible to effectively incorporate calcium phosphate nanoparticles that already comprise one or more therapeutic/diagnostic compounds thus obtaining microparticles of suitable size to generate an inhalation aerosol characterized by high respirability, thus allowing an effective administration and deposition at the pulmonary level in the patient. Once the microparticles are deposited, the water-soluble pharmaceutically carrier matrix dissolves efficiently thus releasing the nanoparticles, which are advantageously get back in dispersed form and with the desired surface and dimensional characteristics and which can therefore effectively convey the therapeutic/diagnostic compounds to the target site.

The inventors have in fact surprisingly discovered that the specific interaction between the pharmaceutically acceptable water-soluble carrier and the calcium phosphate nanoparticle in presence of one or more therapeutic/diagnostic compounds allows on the one hand to prevent aggregation phenomena during the preparation of the microparticle itself, thus contributing to obtaining microparticles with characteristics suitable for their respirability, and on the other hand, it prevents nanoparticles aggregation phenomena after the dissolution of the matrix at the site of pulmonary deposition.

This invention may present in one or more of its aspects one or more of the preferred characteristics listed below, which may be combined with each other according to the application needs.

The powder composition according to the present invention comprises a plurality of microparticles comprising a matrix of at least one water-soluble pharmaceutically acceptable carrier embedding at least one nanoparticle of calcium phosphate comprising one or more therapeutic/diagnostic compounds.

Preferably said at least one nanoparticle has a medium hydrodynamic diameter (Z-medium) determined by laser light diffraction, between 50 and 300 nm, more preferably between 50 and 100 nm. Dimensions in this range have in fact proved to be particularly effective for the absorption of nanoparticles through the lungs and for the delivery of therapeutic/diagnostic compounds to the target site.

Preferably said at least one nanoparticle has a negative surface charge having ξ potential determined by Electrophoretic Light Scattering (ELS) in the range of −10 mV to −41 mV, more preferably from −15 mV to −30 mV. ξ potential values in this range have in fact proved to be particularly effective for the absorption of nanoparticles through the lungs and for the delivery of therapeutic/diagnostic compounds to the target site.

Preferably said at least one nanoparticle comprises it from 0.03% to 32% by weight, with respect to the weight of calcium phosphate, of one or more therapeutic/diagnostic compounds.

Preferably, said nanoparticle encapsule one or more said therapeutic/diagnostic compounds.

Preferably, said one or more therapeutic/diagnostic compounds are selected from the group consisting of: a nucleic acid, a peptide, a protein, an antibody, and a synthetic compound having a molecular weight of less than or equal to 700 Daltons, most preferably chosen in the group consisting of: a nucleic acid, and a peptide.

In the context of the present invention and the subsequent claims, the term "synthetic compound having a molecular weight less than or equal to 700 D" means a so-called small molecule.

In a particularly preferred realization of the present invention, said nucleic acid is selected from the group consisting of: an interference RNA (shRNA, siRNA, microRNA, IncRNA, aptamer), a mimetic RNA (microRNA mimics, IncrNA or other non-coding RNA), a coding RNA (mRNA), a molecule-binding RNA (aptamer, IncRNA), a coding DNA (cDNA) or molecule-binding DNA (aptamer), or a PNA (peptidonucleic acid).

In a further particularly preferred embodiment of the present invention, said peptide is selected in the group that consists of: an L- or D-retro-inverse-peptide (<100 amino acids), an L- or D-retro-inverse-mimetic peptide, (<100 amino acids), or an L- or D-retro-inverse-modified peptide (mimetic), (<100 amino acids).

Synthetic compounds having a molecular weight equal of or not lower than 700 Daltons according to the present invention are, for example, inotropic agents such as Milrinone (211 D), Levosimendan (280 D), Vesnarinone (395 D) or antiarrhythmic agents such as amiodarone (645D) or other drugs that may benefit from a direct release to the heart.

Without wanting to be linked to a particular theory, it is believed that therapeutic/diagnostic compounds such as those described above, and in particular nucleic acids and peptides, in addition to playing their therapeutic/diagnostic role towards the patient surprisingly also contribute in other aspects to the properties of the powder composition according to the present invention. The inventors have in fact found that the therapeutic/diagnostic compounds in the calcium phosphate nanoparticle improve both the aerodynamic characteristics of the microparticles and the interaction between the calcium phosphate nanoparticle itself and the pharmaceutically acceptable water-soluble carrier, thus contributing in one site to the achievement of particularly high respirability values, and to prevent aggregation phenomena between the nanoparticles even after the dissolution of the matrix at the site of pulmonary deposition, thus preserving the possibility for the nanoparticles themselves to be absorbed at the pulmonary level.

Preferably, in the plurality of microparticles of the powder composition according to the present invention the weight ratio (calcium phosphate):(pharmaceutically acceptable carrier) is between 1:2.5 and 1:7, more preferably between 1:2.5 and 1:6, even more preferably between 1:3 and 1:5, optimally between 1:3.5 and 1:4.5.

The inventors surprisingly found that weight ratios between calcium phosphate and a pharmaceutically acceptable water-soluble carrier in these ranges positively influence the aerodynamic properties of microparticles, thus contributing to the achievement of a powder composition endowed with a particularly high respirability.

Preferably said at least one pharmaceutically acceptable carrier is a polyalcohol, such as preferably a compound selected in the group consisting of: mannitol, xylitol, sorbitol, or lactitol.

More preferably said at least one pharmaceutically acceptable carrier is mannitol, which has shown itself to be particularly suitable for the purposes of the present invention thanks to the establishment of a particularly effective interaction with the calcium phosphate nanoparticle which comprises one or more therapeutic/diagnostic compounds, thus capable of contributing to obtaining of a powder composition having aerodynamic properties ideal for the realization of an aerosol by inhalation and, at the same time, able to prevent aggregation phenomena of the nanoparticles themselves both during the preparation of the powder composition, and after the dissolution of the carrier itself at the deposition site. These characteristics allow an effective administration of the nanoparticles by inhalation ensuring a high deposition yield of the same and an adequate absorption of the therapeutic/diagnostic compounds, as well as their effective delivery to the target site.

The powder composition according to the present invention has aerodynamic properties that make it particularly suitable to be used for the administration by inhalation aerosol, and able to effectively reach the site of pulmonary deposition in high yield.

Preferably, the powder composition according to the present invention has a FPF greater than 0.5, more preferably between 0.5 and 0.85, even more preferably greater than or equal to 0.6.

Preferably, the powder composition according to the present invention has an EFPF greater than 0.4.

Preferably, the powder composition according to the present invention has a median volume diameter ($Dv_{50}$) lower than 5.0 μm.

Preferably, the powder composition according to the present invention has a fraction of microparticles with a median aerodynamic mass diameter (MMAD) between 1.0 μm and 5.0 μm.

Aerodynamic characteristics of FPF, EFPF, MMAD, and/or $Dv_{50}$ in the above ranges make the powder composition according to the present invention a composition with high respirability, thus allowing an effective pulmonary deposition of the microparticles before the absorption of the nanoparticles in order to convey the therapeutic/diagnostic compounds to the target site.

Preferably, the microparticles of the composition according to the present invention comprises a quantity of water equal to or less than 6% by weight.

Preferably, the microparticles of the composition according to the present invention have a porous internal structure. More preferably, microparticles with a porous structure have pores with a projection diameter of less than 50 nm, even more preferably between 10 and 50 nm, optimally 20 nm.

In this way, the microparticles according to the present invention show particularly high respirability values and the inventors have observed that the presence of one or more therapeutic/diagnostic compounds in the nanoparticles, preferably nucleic acids and peptides, contributes to the achievement of such a porous structure.

Thus, in a particularly preferred embodiment, the present invention refers to a powder composition comprising microparticles having a porous internal structure and comprising of a matrix of at least one pharmaceutically acceptable water-soluble carrier embedding at least one nanoparticle of calcium phosphate comprising of one or more therapeutic/diagnostic compounds, in which said one or more therapeutic/diagnostic compounds are selected from the group consisting of: a nucleic acid, and a peptide.

In a particularly preferred embodiment, said nucleic acid is selected from the group consisting of: an interference RNA (shRNA, siRNA, microRNA, IncRNA, aptamer), a mimetic RNA (microRNA mimics, IncrNA or other non-coding RNA), a coding RNA (mRNA), a molecule-binding RNA (aptamer, IncRNA), a coding DNA (cDNA) or molecule-binding (aptamer), a PNA (peptidonucleic acid).

In a further particularly preferred embodiment, said peptide is selected from the group consisting of: an L- or D-retro-inverse-peptide (<100 amino acids), or an L- or D-retro-inverse-mimetic peptide (<100 amino acids), or a modified L- or D-retro-inverse-peptide (mimetic), (<100 amino acids).

The composition according to the present invention advantageously allows the administration by aerosol through inhalation of calcium phosphate nanoparticles comprising one or more therapeutic/diagnostic compounds and at the same time to make themselves available at the deposition site after dissolution of the matrix that incorporates them with the right dimensions to be able to effectively convey to the target site the therapeutic/diagnostic compounds in them.

The present invention concerns the powder composition according to the first aspect of the present invention, for use as a medicament.

Under a further and advantageous aspect, the present invention concerns the powder composition according to the first aspect of the present invention, for the use in the treatment of cardiovascular diseases, respiratory diseases, preferably nasal, retronasal and pulmonary, as well as for use as an immunostimulant substance.

The advantages of these additional and advantageous aspects of the invention are the same as those of the powder composition according to the first aspect of the invention.

In an advantageous aspect of the present invention, the powder composition according to the present invention, when used as a medicament, for example, in the treatment of cardiovascular diseases, is administered by inhalation.

The properties of the powder composition according to the present invention make it particularly advantageous to be administered by inhalation.

The present invention, therefore, in a further aspect concerns an inhalation device comprising a container containing a powder composition according to the present invention. Preferably, said container is selected from the group consisting of: a cartridge or a hard capsule, or a blister.

In a further another aspect, the present invention also refers to a powder composition comprising microparticles comprising a matrix of at least one pharmaceutically acceptable water-soluble carrier embedding at least one nanoparticle of calcium phosphate, in which the ratio by weight (calcium phosphate):(pharmaceutically acceptable carrier) is between 1:2.5 and 1:7, more preferably between 1:2.5 and 1:6, even more preferably between 1:3 and 1:5, optimally between 1:3.5 and 1:4.5.

The inventors surprisingly found that the weight ratios between calcium phosphate and a pharmaceutically acceptable water-soluble carrier in these ranges positively influence the aerodynamic properties of microparticles, thus contributing to the achievement of a powder composition endowed with a particularly high respirability.

This composition can be advantageously used for the conveyance of therapeutic/diagnostic compounds of various kinds, for example for the administration by inhalation aerosol.

Conveniently, the powder composition according to the present invention has the additional advantage of being obtainable by a simple and highly reproducible method. This contributes to making the production of the composition according to the present invention economically competitive.

In a further aspect, the present invention therefore concerns a method for the preparation of the powder composition according to the first aspect of the present invention, comprising the steps of:
a) providing a first aqueous dispersion of calcium phosphate nanoparticles comprising one or more therapeutic/diagnostic compounds;
b) dissolving in the dispersion of phase a) at least one pharmaceutically acceptable water-soluble carrier in order to obtain a second aqueous dispersion; and
c) spray-drying the second aqueous dispersion of the step b).

Although the powder composition according to the present invention can also be obtained by other techniques known for this purpose to the skilled person in the field, the method for the preparation of the powder composition according to the present invention advantageously results of simple implementation and high reproducibility, as well as easily scalable, thereby making the preparation of the composition itself competitive and reliable.

The preparation of the first aqueous dispersion according to the step a), can be carried out in any of the ways known for the purpose to the skilled person in the field, for example as reported in the patent application WO 2016/102576.

Preferably, this phase a) comprises the steps of:
1) providing a mixture having a pH in the range of 7 to 10 and comprising an aqueous solution of calcium ions, an aqueous solution of phosphate ions, a solution of citrate ions, and an aqueous solution of one or more therapeutic/diagnostic compounds at a temperature in the range from 20° C. to 40° C. for a period of 30 seconds to 10 minutes;
2) removing the non-reacted ions from the solution obtained in the step 1) obtaining a suspension of calcium phosphate nanoparticles (NP-CaP); and
3) recovering the product of one or more calcium phosphate nanoparticles (NP-CaP) from the suspension of step 2).

Preferably, the aqueous solution of calcium ions of the mixture of step 1) is a solution of calcium chloride with molarity in the range from 20 to 200 mM.

Preferably, the aqueous solution of phosphate ions of the mixture of step 1) is a solution of $Na_2HPO_4$ with molarity in the range from 24 to 240 mM.

Preferably, the temperature of step 1) is in the range from 35 to 40° C., more preferably it is about 37° C.

Preferably, the maintenance time of the mixture of step 1) is about 5 minutes.

Preferably, citrate ions solution is an aqueous solution of sodium citrate having a molarity in the range from 40 to 800 mM.

Preferably, the mixture of step 1) has a pH of about 10.

Preferably, the step 2) of removal of unreacted ions is carried out by means of a dialysis membrane. Preferably, the dialysis membrane is a cellulose membrane with a cut-off less than or equal to 3500 Daltons.

Preferably, the step of removal 2) conducted with dialysis membrane occurs for a time from 5 to 24 hours, preferably for 6 hours.

Preferably, step 3) of recovery of nanoparticles takes place by drying, more preferably by freeze-drying. This advantageously makes it possible to recover the nanoparticles in the solid state.

Once an aqueous dispersion of calcium phosphate nanoparticles comprising of one or more therapeutic/diagnostic compounds according to step a) has been obtained, the method according to this invention provides a step b) in which at least one acceptable pharmaceutically acceptable water-soluble carrier is dissolved in this aqueous dispersion, to obtain a second aqueous dispersion.

In said step b), the ratios by weight between the acceptable water-soluble pharmaceutically carrier and calcium phosphate may vary depending on the final ratio you want to obtain in the microparticles of the powder composition and are preferably those described with reference to the first aspect of the invention.

Preferably, in said second aqueous dispersion the concentration of the solid is between 0.1% w/v and 1.5% w/v, more preferably between 0.15% w/v and 1.0% w/v, and even more preferably between 0.2% w/v and 0.9% w/v, determined at 25° C.

Once the second aqueous dispersion of step b) has been obtained, the method according to the present invention provides for step c) of spray drying said second aqueous dispersion.

Spray-drying is a technique known to the skilled person. Although said step c) of spray drying can be carried out according to any of the spray drying techniques known to the skilled person, the inventors nevertheless surprisingly identified some preferred conditions to carry out this step in order to obtain optimal results.

Preferably, in said step c) of spray drying the air temperature is between 110° C. and 170° C., more preferable between 115° C. and 160° C. and even more preferably between 120° C. and 150° C.

Preferably, in said step c) of spray drying the outlet temperature varies between 45° C. and 95° C., more preferably between 50° C. and 85° C. and, even more preferably between 60° C. and 75° C.

Preferably, in said step c) of spray drying the speed of the drying air flow is between 100 Liters/hour and 850 Liters/hour, more preferably between 300 Liters/hour e 750 Liters/hour, and more preferably between 450 Liters/hour e 700 Liters/hour.

Preferably, in said step c) of spray drying the nozzle is between 0.3 mm and 1.0 mm in diameter, more preferably between 0.5 mm and 0.9 mm and even more preferably between 0.4 mm and 0.7 mm.

Preferably, in said step c) of spray drying the spray rate of the solution is between 2.0 ml/minute and 8.0 ml/minute, more preferably between 2.5 ml/minute and 7.0 ml/minute and even more preferably between 3.0 ml/minute and 5.0 ml/minute.

Preferably, in said step c) of spray drying the suction speed is between 20 $m^3$/hour and 40 $m^3$/hour, more preferably between 25 $m^3$/hour and 38 $m^3$/hour, and even more preferably between 30 $m^3$/hour and 35 $m^3$/hour.

Said conditions of air temperature, outlet temperature, drying air flow rate, nozzle diameter, spray rate and suction speed can be combined in different ways by the skilled person depending on the available equipment and the application or productivity needs, while still allowing to obtain in high yield and in a reproducible way the powder composition according to the present invention.

Therefore, in a further aspect, the present invention refers to a powder composition comprising microparticles comprising a matrix of at least one water-soluble pharmaceutically acceptable soluble carrier embedding at least one nanoparticle of calcium phosphate comprising one or more therapeutic/diagnostic compounds, obtainable by the method according to the present invention.

The invention is now illustrated through some Examples to be understood for illustrative purposes and not limiting of it.

EXPERIMENTAL PART

Example 1

Two aqueous solutions, one of $CaCl_2$) 0.1 M, containing sodium citrate 0.2 M and the other of $Na_2HPO_4$ 0.12 M, were mixed with a fixed mixing volume ratio of 1:1 (v/v) at pH 10.0.

The mixture obtained was kept at 37° C. for 5 minutes, to allow the precipitation of the nanoparticles and then dialyzed overnight to remove unreacted salts. The concentration of the nanoparticles prepared in the aqueous dispersion was about 7.0 mg/ml. The obtained calcium phosphate nanoparticles, analyzed by laser light diffraction, showed an average hydrodynamic diameter (Z-average) of 80±15 nm and ξ potential determined by Electrophoretic Light Scattering (ELS) of −37±2 mV.

Afterward, the dispersion of calcium phosphate nanoparticles thus prepared was diluted with purified water to a solid concentration of 0.5 mg/ml. Mannitol was dissolved in the dispersion of nanoparticles to obtain a ratio in weight calcium phosphate:mannitol of 1:4. The concentration of the solution to be dried, as a dry residue, was 2.5 mg/ml. Then, a spray drying process was carried out with a Büchi B-290 spray dryer, under the conditions reported in Table 1. Finally, the thus obtained powder was recovered from the collection vessel and stored in a sealed glass vial at 20-25° C.

TABLE 1

| T Entrance (° C.) | T Output (° C.) | Flow Atomizer (L/h) | Air Flow ($m^3$/h) | Spray dry rate (ml/min) | Nozzle (mm) |
|---|---|---|---|---|---|
| 125 | 70 | 600 | 35 | 3.5 | 0.7 |

The obtained microparticles were analyzed by scanning electron microscopy and their internal structure analyzed with the SEM/Focus Ion Beam (FIB) particle sectioning technique.

The morphology of the microparticles and the surface characteristics of the powders were studied by scanning electron microscopy SEM/Focus Ion Beam (FIB).

The instrument employed was a scanning field emission electron microscope—Focused ion beam (FESEM-FIB, Auriga Compact, Zeiss, Germany) equipped with a field emission microscope at different resolutions and working distances.

Samples were prepared by placing 1-2 mg of microparticles in a carbon tape on an aluminum stub. The microparticle morphologies were observed using a Phenom-Prox SEM (Phenom-World, The Netherlands) with the detector in secondary electron mode with an operating voltage of 1 kV and an operating pressure of 1 Pa.

In order to study the internal structure of microparticles embedding CaP for porosity analysis, a Zeiss Auriga FIB-SEM (Zeiss, Germany) was employed to cut particles by course-line engraving with an operating voltage of 1 kV and a current of 1 nA, followed by FIB (fine-line) polishing with an operating voltage of 30 kV and a current of 100 pA.

During FIB cutting, land images were taken in SEM mode with the same SEM operating conditions after FIB processing with magnifications between 5000× and 70,000×.

Figure 1A:
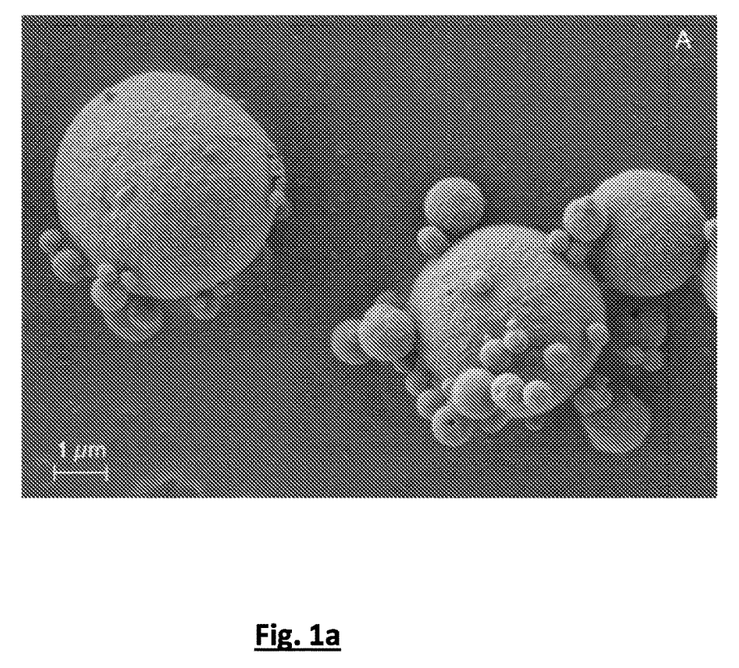
Figure 1B:
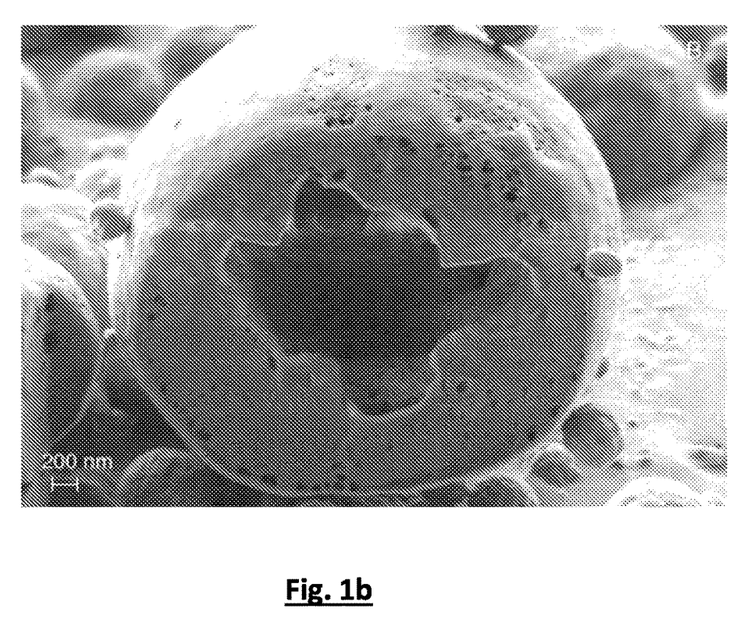
Figure 2A:
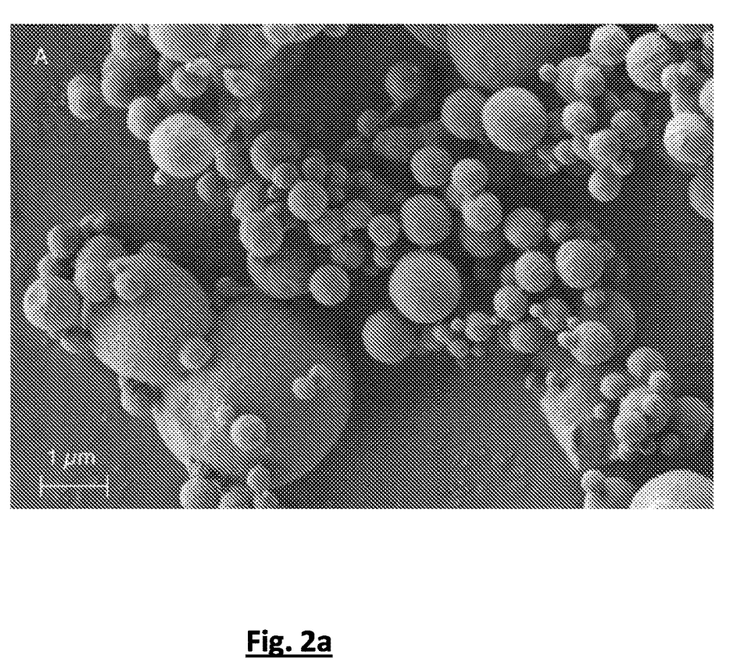
Figure 2B:
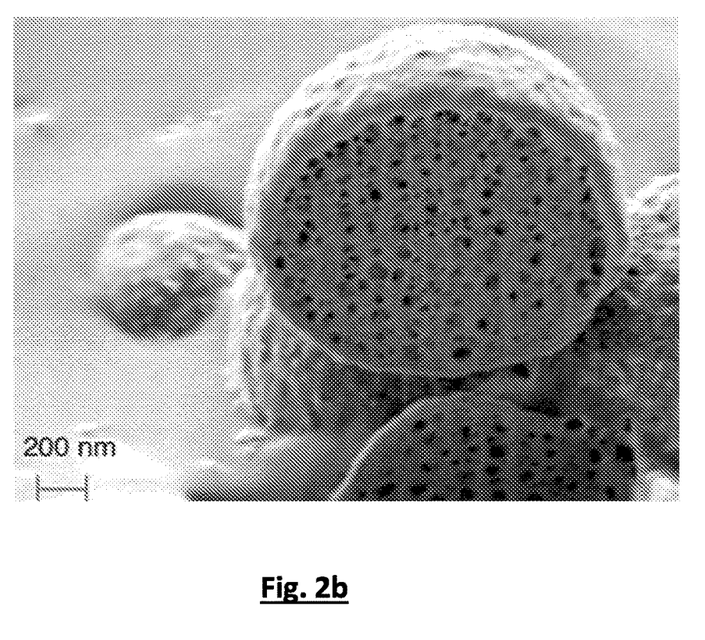

FIG. 1a shows a scanning microphotograph of the microparticles obtained, while FIG. 1b shows a dissected microparticle.

It was possible to note that the obtained microparticles had a substantially spherical shape. The image obtained with the SEM/FIB particle sectioning technique also showed the presence of an internal structure characterized by a large cavity in the center, with a few smaller voids scattered around it.

The particles were also characterized in order to determine their dimensional characteristics ($Dv_{10}$, $Dv_{50}$, $Dv_{90}$), the residual water content, the aerodynamic behavior (EF, FPF), as well as the stability of the nanoparticles after dissolution of mannitol matrix.

As for the dimensional characteristics, the values of $Dv_{10}$, $Dv_{50}$, $Dv_{90}$ were determined by a laser scattering technique and calculated from the dimensional distribution of the measured diameters.

The in vitro aerodynamic behavior of the microparticles was measured with the Fast-Screening Impactor; a hard capsule was loaded with 40 mg of powder, inserted into the RS01® inhaler device (Plastiape, ITA) and the powder was "inhaled" in vitro by applying an air velocity of 60 L/min. The powder was successfully emitted by the device and the EF and FPF values were determined, the first by measuring the weight of the device loaded with the capsule before and after the emission, while FPF was determined by measuring the amount of dust deposited in the Fast screening on stage 2 called Fine Fraction which retains particles smaller than 5 μm which in turn passed through stage 1 which retained particles larger than 5 μm.

The water content of the microparticles was determined by thermogravimetric analysis (TGA).

The stability of the size of the nanoparticle after mannitol dissolution was measured by the following method: 2.5 mg of powder were dissolved in 1 ml of purified water gently shaking to obtain a concentration of 0.5 mg/ml of calcium phosphate. The suspended nanoparticles were then analyzed to determine their average hydrodynamic diameter (Z-medium) and ξ potential, with the same methods described above.

Table 2 shows the results obtained by these characterizations.

It was thus possible to notice that the obtained microparticles showed dimensions ($Dv_{10}$, $Dv_{50}$, $Dv_{90}$) and respirability characteristics (EF, FPF) such as to make them suitable for use as an inhalation aerosol. Moreover, from the comparison between the average hydrodynamic diameter (Z-medium) and the potential of the nanoparticles before the incorporation into the mannitol matrix and after the dissolution of the matrix, it was possible to find a substantial coincidence of values, attesting the absence of significant nanoparticles aggregation phenomena, and therefore the maintenance of properties that allows the nanoparticles to be absorbable at the pulmonary level.

Example 2

Calcium phosphate nanoparticles comprising the mimetic peptide (MP; 11 AA, MW: 1326 Da, a-helix structure) intended for the binding of the Cav82 subunit of the calcium channel (European Patent Application No EP 3 107 933), were prepared following the procedure of example 1, with the difference of adding the mimetic peptide to a concentration of 0.6 mg/ml in the solution of $Na_2HPO_4$ 0.12 M. The obtained calcium phosphate nanoparticles comprising the peptide showed an average hydrodynamic diameter (Z-mean) of 105±20 nm and a ξ potential of −25±7 mV. The peptide content, expressed as peptide quantity on calcium phosphate amount, measured by HPLC, was 6.0±2.0% w/w.

For the quantification of the peptide, an HPLC gradient method was used and a C18 chromatographic column with 5 μm porosity was used. To 1 ml of CaP dispersion comprising the peptide, 1 ml of HCl 0.1N was added. It was gently shaken to complete the dissolution and obtain a clear solution. The solution was transferred to a clear glass vial of 1.5 ml and HPLC analysis was performed using the Agilent 1200 LC Series tool (Agilent Technologies, USA).

The same spray dryer as in Example 1 was used to manufacture microparticles embedding calcium phosphate nanoparticles including peptide (dpCaPs/MP). Mannitol was dissolved in the dispersion of nanoparticles to obtain a ratio in weight of calcium phosphate:mannitol of 1:4, so that the solution for dry spraying contained 2.0 mg/ml of mannitol and 0.5 mg/ml of calcium phosphate nanoparticles comprising the peptide. The mixture was shaken for a few minutes at room temperature to perform the dissolution of the carrier. This feed solution was spray-dried under the same conditions as in Example 1. Finally, the recovered powder was stored at room temperature in sealed vials. The yield of the drying process was about 65%. The obtained microparticles contained 0.5% w/w MP peptide as measured by the same HPLC method described in Example 1, except for sample preparation: 20 mg of microparticles were dissolved in 2 ml of HCl 0.1 N. After 15 minutes and at completely dissolution, the clear solution was analyzed by HPLC.

The microparticles obtained were also characterized as in Example 1.

In FIG. 2*a* a scanning electron microphotograph of the obtained microparticles is shown, while in FIG. 2*b* a microparticle dissected with the FIB/SEM technique is shown, according to the methods described in Example 1, while the results of the other characterizations carried out are reported in Table 2.

From the obtained SEM images reported in FIGS. 2*a* and 2*b* it was possible to observe that the also the microparticles obtained in Example 2 showed a substantially spherical shape. The internal structure, however, differs substantially from that of the microparticles according to Example 1 and had an internal porous structure. Numerous small cavities with a diameter of 2 to 20 nm, which appear in FIG. 2*b* as a grid, were in fact revealed by FIB/SEM analysis. These numerous pores determined an internal structure of the microparticles that can be defined as alveolar type, which to the knowledge of the inventors has never been observed before in microparticles such as those according to the present invention. It was also noted that the microparticles according to example 2 showed significantly better aerodynamic properties than the microparticles in example 1 (see table 2) and allowed to obtain, after the dissolution of the mannitol matrix, the calcium phosphate nanoparticles in their original size, as it is evident by comparing the values of the dimensions of the nanoparticles before and after the incorporation (Table 2, columns "Original nanoparticles" and "Redispersed nanoparticles"). These microparticles were also characterized regarding the distribution of the aerodynamic diameter giving a value of MMAD, which was 2.6 μm with geometric standard deviation (GSD) of 1.72.

Example 3

Calcium phosphate nanoparticles were prepared as reported in Example 1, adding in the phosphate ions solution 0.014 mg/ml of mimetic microRNA of miR-133 (Qiagen, #339174), which is a well-known therapeutic compound for cardiovascular disease capable of playing a key role in the remodeling of cardiomyocytes. The calcium phosphate nanoparticles comprising the micro-RNA obtained showed a mean hydrodynamic diameter (Z-mean) of 1900±50 nm, signal of the presence of nanoparticle aggregates, a potential of −17±5 mV, and a microRNA content of % by weight, in relation to the weight of calcium phosphate.

Subsequently, the microparticles embedding said nanoparticles (dpCaPs/micro-RNA) were prepared by spray drying.

For this purpose, mannitol was dissolved in the dispersion of nanoparticles in order to obtain a ratio in weight of calcium phosphate:mannitol of 1:4, so that the solution for dry spraying contained 2.0 mg/ml of mannitol and 0.5 mg/ml of calcium phosphate nanoparticles comprising micro-RNA. The as obtained dispersion was shake for a few minutes at room temperature to allow the dissolution of the vector. This feed solution was spray-dried under the same conditions as in Example 1. The produced microparticles were stored at room temperature in sealed bottles. The yield of the spray drying procedure was about 70%. The as obtained microparticles contained 0.006% w/w of microRNA.

A digital PCR method was used for the quantification of microRNA. 1 ml of CaP suspension (n=4), was centrifuged at 20,000 rpm for 15 minutes. 0.1 ml of supernatant was withdrawn while the pellet was resuspended in 1 ml of water from which 0.1 ml was withdrawn. 0.1 ml of total suspension, pellet and supernatant were then subjected to acid dissolution by HCl 0.1 N followed by vortexing for 5 minutes. RNA was extracted from each sample, retrotranscribed and the microRNA quantized by digital PCR.

The obtained microparticles were also characterized as in Example 1.

Figure 3A:
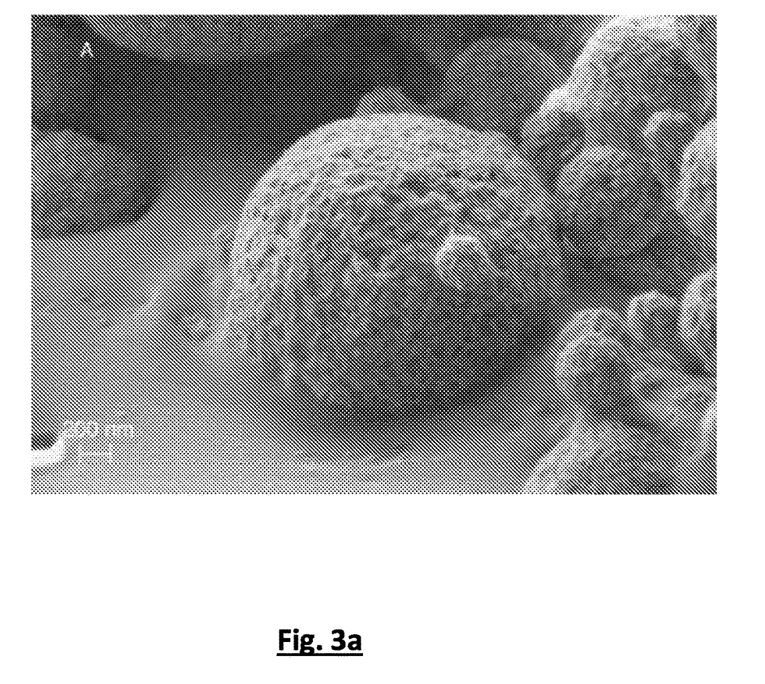
Figure 3B:
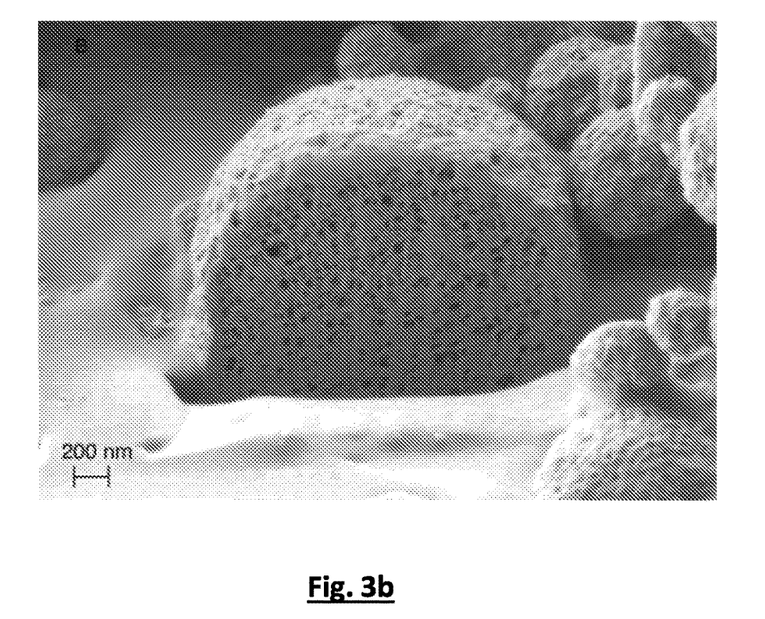

In FIG. 3a a is shown a scanning microphotograph of the obtained microparticles, while in FIG. 3b a dissected microparticle with the FIB/SEM technique is shown, according to the methods described in Example 1, while the results of the other characterizations are reported in Table 2.

From the scanning electron microscope analysis (FIG. 3a) it was possible to detect that the microparticles according to example 3 showed a substantially spherical shape and a wrinkled outer surface and had a median volume diameter of less than 5 microns. The dissected microparticles (FIG. 3b) also showed a porous internal structure of alveolar type, with several small pores with diameter of 10-50 nm. As can be seen from the data reported in Table 2, the inventors also found that these microparticles, once dissolved the mannitol matrix were surprisingly able to restore nanoparticles having dimensions around 250 nm, disaggregating the aggregates of initial nanoparticles obtained at the end of the preparation of the nanoparticles themselves. The inventors believe that mannitol therefore surprisingly also played an active molecular role in the disaggregation of calcium phosphate nanoparticles.

Example 4

Example 2 was repeated by adding in the phosphate ions solution, instead of the mimetic peptide MP, 0.15 mg/ml of R7W peptide (R7W-MP) (19 amino acids, MW: 2605.9, a-helix structure). The yield of the drying process was 84.4%. The R7W-MP peptide content of the produced microstructure was 0.25% w/w.

Figure 4A:
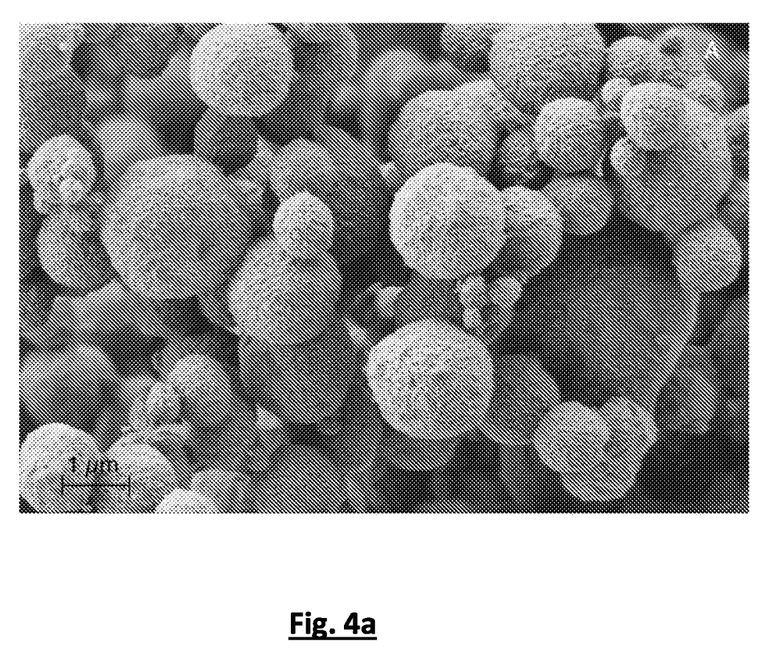
Figure 4B:
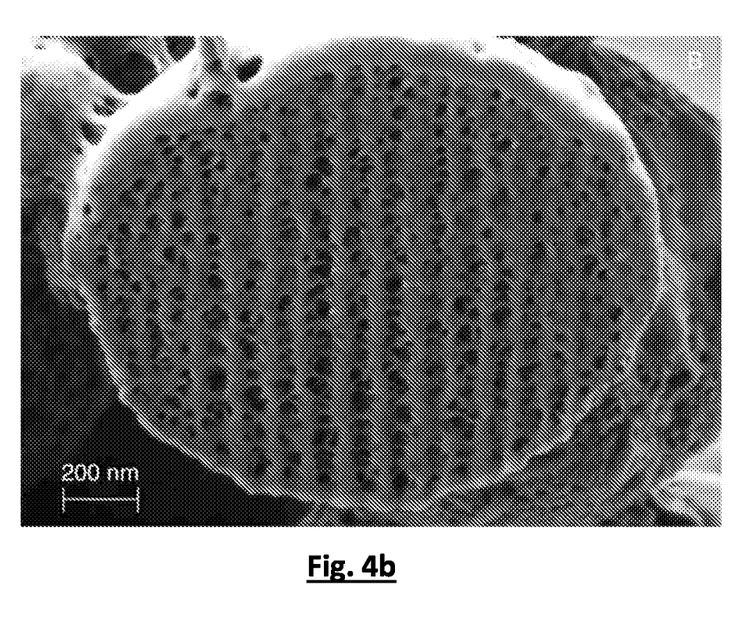

In FIG. 4a a is shown a microphotograph by scanning electron microscope of the obtained microparticles, while in FIG. 4b a dissected microparticle with the FIB/SEM technique is shown, according to the methods described in Example 1, while the results of the other characterizations are shown in Table 2.

Also in this case, scanning electron microscopy showed microparticles having a spherical shape (FIG. 4a) and with rough surface, with an average size in the range from 200 nm to 2 μm. The SEM/FIB (FIG. 4b) allowed to highlight also in this case the presence of a porous internal structure of alveolar type, with pores having a diameter of 20 nm or less. The inventors believe that this internal structure derives from the interaction between the nanoparticles comprising the R7W-MP peptide and the microparticle matrix, similarly to what was observed in examples 2 and 3, in which the nanoparticles also comprises a therapeutic/diagnostic compound of macromolecular structure.

Example 5

Example 2 was repeated adding in the phosphate ions solution, instead of the mimetic peptide, 0.15 mg/ml of Influenza Hemagglutinin Peptide (HA) (YPYDVPDYA, molecular weight 1102.05 Da, having a less organized secondary structure than MP and R7W-MP, microRNA). The yield of the drying process was 80%. The content of HA peptide in the produced microstructure was 0.25% w/w.

Figure 5A:
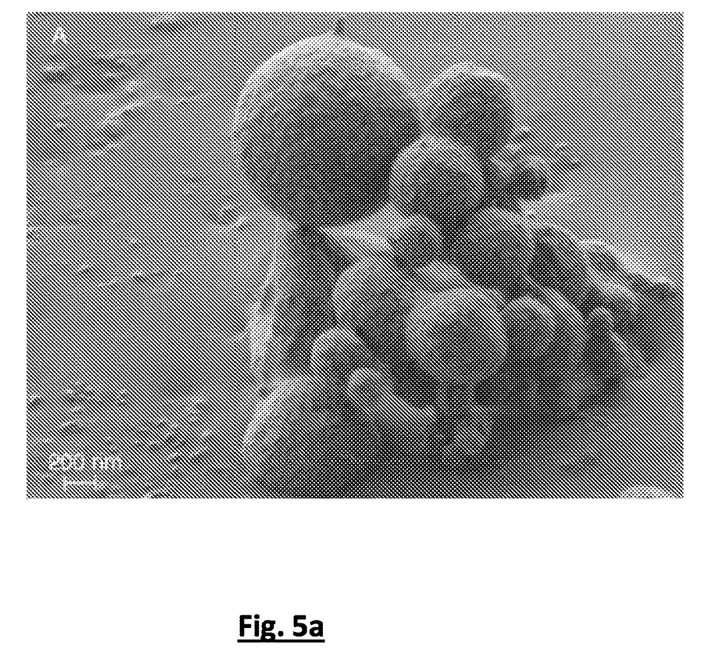
Figure 5B:
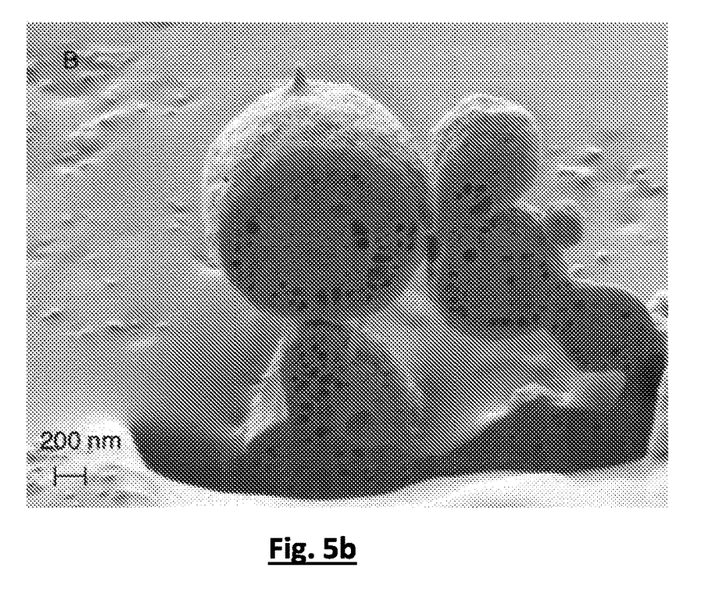
Figure 6A:
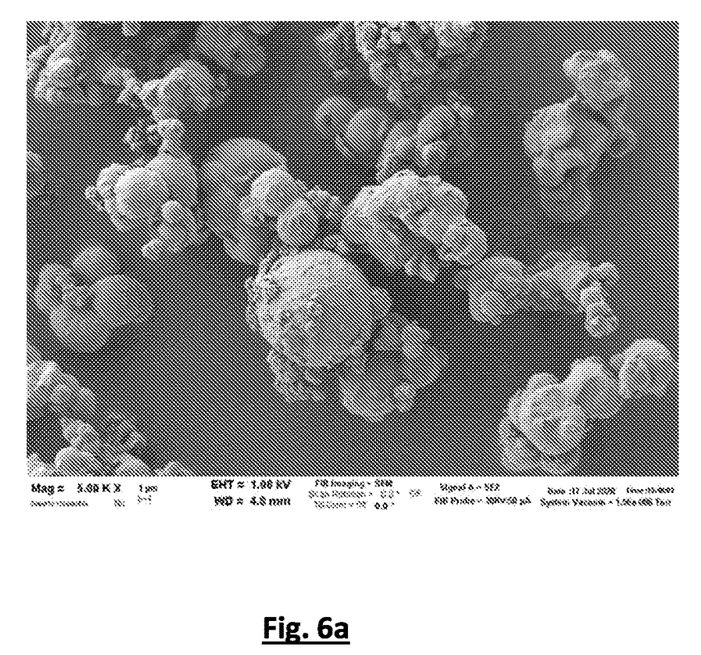
Figure 6B:
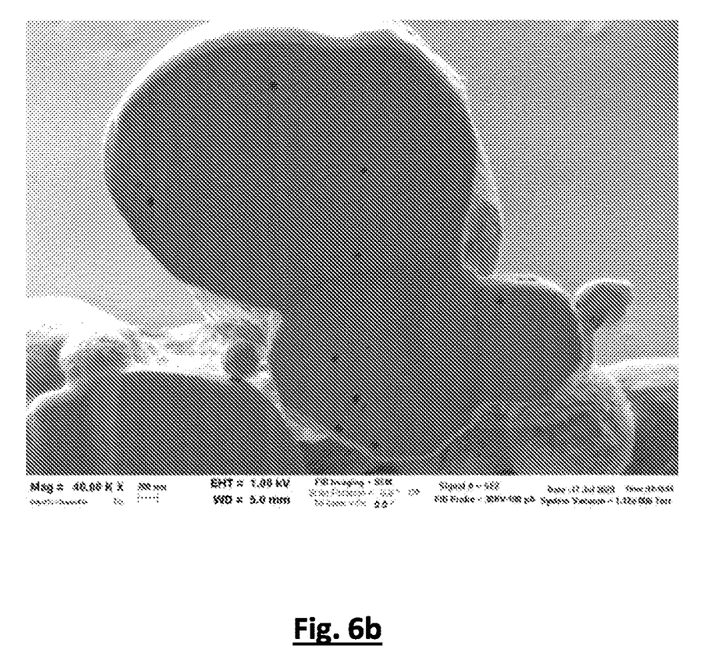

In FIG. 5a a is shown a scanning microphotograph of the obtained microparticles, while in FIG. 5b a microparticle dissected with the FIB/SEM technique is shown, according to the methods described in Example 1, while the results of the other characterizations are shown in Table 2.

Also in this case, scanning electron microscope analysis showed microparticles having a spherical shape (FIG. 5a). The SEM/FIB (FIG. 5b) allowed also to highlight the presence of a porous internal structure with pores having a diameter of nm or less, in which the pores appear, however, less regularly distributed than in examples 2-4. Despite this difference, the microparticles still showed high in vitro respirability values and the ability to restore nanoparticles after dissolution of the mannitol matrix, maintaining substantially unchanged the dimensional and surface charge properties (see Table 2).

Example 6

Example 2 was repeated, using for the preparation of the microparticles a ratio by weight calcium phosphate:mannitol of 1:6, instead of 1:4 and using for the spray drying phase a feed solution containing 11.5 mg/ml of mannitol and 1.9 mg/ml of calcium phosphate nanoparticles comprising the mimetic peptide.

In Table 2 the data of the characterizations are shown.

The microparticles of Example 6 showed high respirability, in line with that of microparticles according to Example 2.

TABLE 2

| Example | Therapeutic-diagnostic compound comprised in nanoparticles compared to calcium phosphate[1] (% w/w) | Therapeutic-diagnostic compound comprised in microparticles[2] (% w/w) | Water content of microparticles[3] (w/w %) | EF microparticles[4] | FPF microparticles[5] | Diameter volume of microparticles[6] | | | Originating nanoparticles[7] | | Redispersed nanoparticles[8] | |
|---|---|---|---|---|---|---|---|---|---|---|---|---|
| | | | | | | $D_{v10}$ (μm) | $D_{v50}$ (μm) | $D_{v90}$ (μm) | Average hydrodynamic diameter (Z-medium) | ζ potential (mV) | Average hydrodynamic diameter (Z-medium) | ζ potential (mV) |
| 1 | — | — | 1.5 ± 0.5 | 0.85 | 0.58 | 1.4 ± 0.3 | 3.4 ± 1 | 8.4 ± 0.7 | 80 ± 15 | −37 ± 2 | 85 ± 5 | −35 ± 2 |
| 2 | 6.0 | 0.5 | 2.0 ± 0.5 | 0.92 | 0.80 | 1.2 ± 0.2 | 2.0 ± 0.4 | 4.5 ± 0.5 | 105 ± 20 | −25 ± 7 | 125 ± 10 | −25 ± 5 |
| 3 | 0.03 | 0.006 | 1.0 ± 0.5 | 0.89 | 0.65 | 1.3 ± 0.2 | 2.3 ± 0.6 | 5 ± 0.5 | 1900 ± 50 | −17 ± 5 | 250 ± 15 | −17 ± 3 |
| 4 | 1.5 | 0.25 | 1.5 ± 0.5 | 0.86 | 0.68 | 1.1 ± 0.2 | 2.1 ± 0.4 | 4.5 ± 0.5 | 120 ± 15 | −20 ± 3 | 60.7 ± 5 | −24.5 ± 2 |
| 5 | 1.25 | 0.25 | 1.0 ± 0.5 | 0.87 | 0.67 | 2 ± 0.2 | 2.1 ± 0.2 | 4.8 ± 0.5 | 160 ± 25 | −25 ± 2 | 154 ± 10 | −23 ± 5 |
| 6 | 6.0 | 0.9 | 1.7 ± 0.2 | 0.82 | 0.60 | 1.2 ± 0.2 | 1.8 ± 0.5 | 4.5 ± 0.3 | 80 ± 10 | −25 ± 2 | 68 ± 10 | −20 ± 3 |

[1] indicates the percentage by weight of the therapeutic-diagnostic compound in relation to the total weight of the nanoparticle;
[2] indicates the percentage by weight of therapeutic-diagnostic compound compared to the total weight of the microparticle;
[3] indicates the percentage by weight of water compared to the total weight of the microparticle;
[4] indicates the EF value of the powder composition;
[5] indicates the FPF value of the powder composition;
[6] indicates the volume diameter value;
[7] the columns below refer to the values of average hydrodynamic diameter and ζ potential of the original nanoparticles, before their incorporation into the microparticles;
[8] the columns below refer to the values of average hydrodynamic diameter and ζ potential of nanoparticles after dissolution of the microparticles matrix;

(1) indicates the percentage by weight of the therapeutic-diagnostic compound in relation to the total weight of the nanoparticle;
(2) indicates the percentage by weight of therapeutic-diagnostic compound compared to the total weight of the microparticle;
(3) indicates the percentage by weight of water compared to the total weight of the microparticle;
(4) indicates the EF value of the powder composition;
(5) indicates the FPF value of the powder composition;
(6) indicates the volume diameter value;
(7) the columns below refer to the values of average hydrodynamic diameter and potential of the original nanoparticles, before their incorporation into the microparticles;
(8) the columns below refer to the values of average hydrodynamic diameter and potential of nanoparticles after dissolution of the microparticles matrix;

The invention claimed is:

1. A powder composition for delivery by inhalation comprising microparticles having a volume diameter of less than 10 μm and a porous internal structure, the microparticles comprising a polyalcohol matrix embedding at least one nanoparticle of calcium phosphate having a volume diameter of less than 300 nm; wherein said at least one nanoparticle comprises one or more therapeutic compounds; wherein the weight ratio calcium phosphate nanoparticle:polyalcohol is between 1:2.5 and 1:7; and wherein the composition has a fraction of microparticles with an aerodynamic diameter between 0.5 and 5.0 microns (FPF) wherein FPF is the FPD/ED ratio, in which:

"aerodynamic diameter" is the diameter of a sphere of unit density that has the same sedimentation rate as the actual particle under consideration, measured by applying the method described in the European Pharmacopoeia 9.0 chapter 2.9.18;

FPD is the quantity of fine particles (particles with an aerodynamic diameter of less than 5.0 μm) of the powder composition; and ED is the amount of pre-dosed powder composition emitted by a dry powder inhaler, measured according to the method of the European Pharmacopoeia 11.0 chapter 2.9.18.

2. The powder composition comprising microparticles according to claim 1, wherein said one or more therapeutic compounds are selected from the group consisting of: a nucleic acid, a peptide, a protein, an antibody, and a synthetic compound having a molecular weight not exceeding 700 Daltons, wherein the synthetic compound is selected from the group consisting of inotropic agents, and antiarrhythmic agents.

3. The powder composition comprising microparticles according to claim 1, wherein the microparticles of the composition have a median volume diameter ($Dv_{50}$) of less than 5.0 μm.

4. The powder composition comprising microparticles according to claim 1, wherein said porous internal structure comprises pores having a diameter less than 50 nm, determined by Scanning Electron Microscopy.

5. The powder composition comprising microparticles according to claim 1, wherein the polyalcohol is selected from the group consisting of mannitol, xylitol, sorbitol, and lactitol.

6. The powder composition comprising microparticles according to claim 5, wherein the polyalcohol is mannitol.

* * * * *